United States Patent [19]

Druliner

[11] Patent Number: 5,449,807

[45] Date of Patent: Sep. 12, 1995

[54] CATALYZED VAPOR PHASE HYDROCYANATION OF DIOLEFINIC COMPOUNDS

[75] Inventor: Joe D. Druliner, Newark, Del.

[73] Assignee: E. I. Du Pont de Nemours and Company, Wilmington, Del.

[21] Appl. No.: 342,195

[22] Filed: Nov. 18, 1994

[51] Int. Cl.⁶ .......................................... C07C 253/10
[52] U.S. Cl. ...................................................... 558/338
[58] Field of Search ........................................... 558/338

[56] References Cited

U.S. PATENT DOCUMENTS

| | | | |
|---|---|---|---|
| 3,496,215 | 2/1970 | Drinkard et al. | 558/338 |
| 3,496,217 | 2/1970 | Drinkard, Jr. et al. | 558/338 |
| 3,496,218 | 2/1970 | Drinkard, Jr. et al. | 558/338 |
| 3,547,942 | 12/1970 | Godefroi et al. | 260/309 |
| 3,574,701 | 4/1971 | Kominami et al. | 260/465.3 |
| 3,578,695 | 5/1971 | Milberger et al. | 260/465.3 |
| 3,584,029 | 6/1971 | Kominami et al. | 260/465.3 |
| 3,766,237 | 10/1973 | Chia et al. | 260/465.3 |
| 3,773,809 | 11/1973 | Walter et al. | 558/338 |
| 3,775,461 | 11/1973 | Drinkard, Jr. et al. | 558/338 X |
| 3,776,231 | 11/1973 | Gosser et al. | 558/338 X |
| 3,798,256 | 3/1974 | King et al. | 558/338 |
| 3,865,864 | 2/1975 | Nakajima et al. | 260/465.3 |
| 3,869,500 | 3/1975 | Kominami et al. | 260/465.3 |
| 3,925,445 | 12/1975 | King et al. | 558/338 |
| 4,371,474 | 2/1983 | Rapoport | 558/338 |
| 4,705,881 | 11/1987 | Rapoport | 558/338 |

FOREIGN PATENT DOCUMENTS 6916495 5/1971 Netherlands.

OTHER PUBLICATIONS

Baker, M. J. et al, "Chelating Disphoshite Complexes of Nickel(O) and Platinum(O): Their Remarkable Stability and Hydrocyanation Activity", *J. Chem. Soc., Chem. Commun.*, 803–804 (1991).

*Primary Examiner*—Joseph Paul Burst

[57] ABSTRACT

A catalyzed vapor phase process for the hydrocyanation of acyclic diolefinic compounds to olefinic nitriles in which the olefinic double bond is not conjugated to the triple bond of the cyano group, wherein a catalyst composition comprising at least one bidentate phosphite ligand and zero-valent nickel is used.

15 Claims, No Drawings

CATALYZED VAPOR PHASE HYDROCYANATION OF DIOLEFINIC COMPOUNDS

FIELD OF THE INVENTION

This invention generally relates to a gas phase process for the hydrocyanation of diolefinic compounds to produce nonconjugated acyclic nitriles. In particular, the invention relates to a gas phase process for the hydrocyanation of diolefinic compounds to produce nonconjugated acyclic nitriles utilizing zero-valent nickel and a bidentate phosphite ligand.

BACKGROUND OF THE INVENTION

Catalytic hydrocyanation systems, particularly pertaining to the hydrocyanation of olefins, are known in the art. For example, liquid phase systems useful for the hydrocyanation of butadiene to form pentenenitriles (PN) are known in the art, e.g., U.S. Pat. No. 3,766,237. As used in that patent, and as will be used herein, the term "pentenenitrile" is intended to mean a cyanobutene. Likewise, "butenenitrile" means cyanopropene. The pentenenitriles so formed are further subjected to hydrocyanation and, in some cases isomerization, to form adiponitrile (ADN), a commercially important material in the manufacture of nylon. Bidentate phosphite ligands complexed to zero-valent nickel and platinum are known to be useful in the liquid phase hydrocyanation of butadiene, as described by Baker et al., *J. Chem. Soc.*, Chem. Commun., 1991, pages 803–804.

The overwhelming majority of prior art processes for the hydrocyanation of butadiene are conducted in the liquid phase, with all attendant waste disposal problems. Previous approaches toward carrying out gas phase hydrocyanation of olefinic compounds have usually started with monoolefinic, not diolefinic, compounds and have given rise primarily to saturated products, which could not be further hydrocyanated. For example, Dutch Patent 6916495 teaches that pivalonitrile is prepared by reaction of HCN and isobutylene over $Al_2O_3$ or $SiO_2$ catalysts; U.S. Pat. No. 3,584,029 teaches that propionitrile is prepared by reaction of HCN with ethylene over catalysts containing Ni salts, $H_3PO_4$ and $Al_2O_3$; and U.S. Pat. No. 3,547,942 discloses the reaction of HCN and butadiene in the gas phase over a mixed metal catalyst containing copper chromite and activated copper chromite, which does yield a mixture of pentenenitriles, with 77–82% selectivities to 3-pentenenitrile and 4-pentenenitrile. However, the reaction of U.S. Pat. No. 3,547,942 also requires a co-feed of HCl.

Several patents teach that reaction of HCN with butadiene, ethylene, propylene or butenes, and additionally with air or oxygen in the gas phase, over various supported metal-containing catalysts give rise to cyanated olefinic products. However, in the olefinic products so produced the olefinic double bond is usually conjugated with the triple bond of the cyano group, and, therefore, substantially useless for the production of adiponitrile. For example, see:

U.S. Pat. No. 3,865,863, Asahi, Feb. 11, 1975

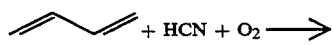

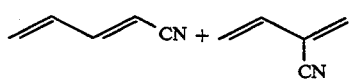

U.S. Pat. No. 3,574,701, Asahi K. K. K., Apr. 13, 1971

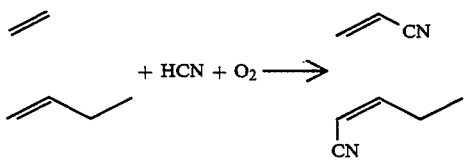

U.S. Pat. No. 3,578,695, Standard Oil, May 11, 1975

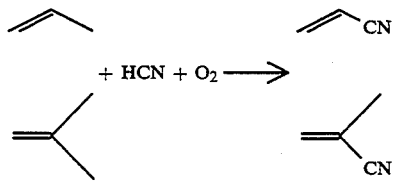

U.S. Pat. No. 3,869,500, Asahi, Mar. 4, 1975

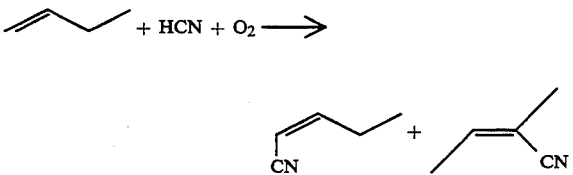

The present invention provides a catalyzed gas phase process for the hydrocyanation of diolefinic compounds which is rapid, selective, and efficient. While certain solvents or diluents can be used in this process, they can be eliminated altogether. Furthermore, the catalyst is utilized as a stationary solid phase, which can reduce the costs of catalyst synthesis, recovery, and recycle, as well as the disposal cost of byproduct waste. A corollary benefit is the reduction of the cost of capital equipment needed for the process. Other objects and advantages of the present invention will become apparent to those skilled in the art upon reference to the detailed description of the invention which hereinafter follows.

SUMMARY OF THE INVENTION

The present invention provides a process for the gas-phase hydrocyanation of diolefinic compounds comprising, reacting an acylic aliphatic diolefinic compound, preferably butadiene, with HCN in the gas phase within a temperature range of from about 135° C. to about 170° C. in the presence of a supported catalyst composition comprising zero-valent nickel and at least one bidentate phosphite ligand selected from the group consisting of compounds represented by Formulas I and II:

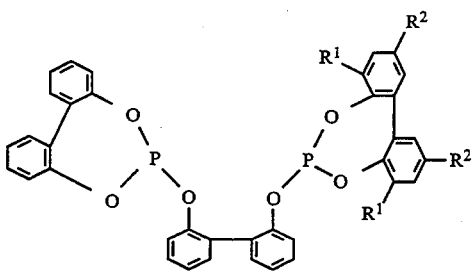

Formula I wherein
each $R^1$, independently, is a secondary or tertiary hydrocarbyl of 3 to 12 carbon atoms;
each $R^2$, independently, is H, a $C_1$ to $C_{12}$ alkyl, or $OR^3$, wherein $R^3$ is $C_1$ to $C_{12}$ alkyl; and

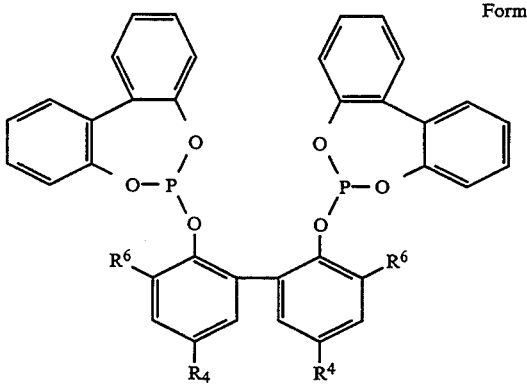

Formula II wherein
each $R^4$, independently, is a tertiary hydrocarbon of up to 12 carbon atoms, or $OR^5$, wherein $R^5$ is a $C_1$ to $C_{12}$ alkyl; and
each $R^6$, independently, is a tertiary hydrocarbon of up to 12 carbon atoms, to produce acyclic, preferably 3- and 4-pentenenitriles, in which the olefinic double bond is not conjugated with the cyano group.

In the above definitions for both Formula I and Formula II, the terms "secondary" and "tertiary" refer to the carbon atom attached to the aromatic ring. In addition, for purposes of the present disclosure and claims, the terms "alkenenitrile", "pentenenitrile", and "butenenitrile" are intended to mean, respectively, a cyanoalkene in which the carbon atom of the cyano group is the first carbon; a cyanobutene; and a cyanopropene.

When 1,3-butadiene (BD) is utilized as the starting material, this gas phase hydrocyanation process produces a mixture of pentenenitriles (PN) consisting essentially of 3-pentenenitrile (3PN), 4-pemenenitrile (4PN) and 2-methyl-3-butenenitrile (2M3BN). Small amounts of dinitriles (DN) and of a dimer of 1,3-butadiene, 2-vinylcyclohexene (VCH) also are sometimes produced.

DETAILED DESCRIPTION OF THE PREFERRED EMBODIMENTS

Catalysts useful in the practice of the present invention consist essentially of the bidentate phosphite complexes supported on carriers of silica, alumina, carbon, or other suitable supports. Commonly used techniques for treatment of supports with metal catalysts can be found in B. C. Gates, Heterogeneous Catalysis, Vol. 2, pp. 1–29, Ed. B. L. Shapiro, Texas A & M University Press, College Station, Tex., 1984. Alternately, a given support can be prepared with a uniformly dispersed coating of zero-valent nickel metal and then can be treated with a bidentate phosphite ligand. Typically, in accordance with this invention, the zero-valent nickel catalysts are dispersed on silica, alumina or carbon supports at concentrations sufficient to produce a supported catalyst composition containing 0.3% wt. to 1.0% wt. Ni.

The catalysts are then loaded into tubular reactors, and a gaseous diolefinic compound, e.g., butadiene, and HCN is passed continuously over the solid catalysts at temperatures sufficiently high to maintain the starting materials as well as the reaction products in the gas phase. The preferred temperature range is from about 140° C. to about 160° C., most preferably from about 145° C. to about 150° C. The temperature must be high enough to maintain all the reactants and products in the gas phase but low enough to prevent deterioration of the catalyst. The particular preferred temperature depends to some extent on the catalyst being used, the diolefinic compound being used, and the desired reaction rate. The operating pressure is not particularly critical and can conveniently be from about 1–10 atmospheres (101.3 to 1013 kPa). No practical benefit is obtained when operating above the upper limit of this pressure range.

HCN and/or diolefinic compound starting materials can be delivered as a neat vapor or as a preheated solution in a solvent, such as acetonitrile or toluene. Under atmospheric pressure, using nitrogen or another inert gas as a carrier, temperatures of from about 140°–150° C. are typically used. Nitrogen is preferred because of its low cost. Gaseous oxygen, water vapor, or other gaseous substance which could react with the HCN, the zero-valent nickel catalyst, or the starting diolefinic compound should be avoided. The reaction products are liquid at room temperature and are conveniently recovered by cooling. Branched 2-methyl-3-butenenitrile can be separated from linear 3-pentenentrile and 4-pentenenitrile by distillation.

Zero-valent nickel is known to the art and can be made in a number of ways. Most common zero-valent nickel species, which can be used to form the catalytic compositions useful in the present invention, are derived from Ni(0) complexes containing o-tritolylphosphite, p-tritolylphosphite, cyclooctadiene, and ethylene. Ni(0) can also be prepared by reduction of Ni(II) compounds with molecular hydrogen, or other reducing agents, in the presence of appropriate ligands (e.g., where Ni(NO₃)₂ is reduced by H₂ to provide Ni(0) on silica gel). Moreover, Ni(0) complexes containing bidentate ligands can be prepared from reduction of Ni(II) compounds (e.g., where Ni(ligand "A")(ethylene) is prepared) and Ni metal and a bidentate ligand. Other zero-valent nickel species known to those skilled in the art can be successfully used as well.

The actual catalyst is a complex of zero-valent nickel with the bidentate ligand, which is formed when those two materials are combined. An effective catalyst requires at least one mole of bidentate ligand for one gram-atom of zero-valent nickel.

The diolefinic compound reactants used in this invention include primarily conjugated diolefins containing from 4 to 10 carbon atoms; for example 1,3-butadiene and cis and trans-2,4-hexadienes. Butadiene is especially preferred by reason of its commercial importance in the production of adiponitrile. Other suitable diolefinic compounds include diolefinic compounds substituted with groups which do not deactivate the catalyst, for example, cis and trans-1,3-pentadienes.

The following Formulas III and IV illustrate suitable representative starting diolefinic compounds; and Formulas V, VI, and VII represent the products obtained from 1,3-butadiene and HCN.

$$CH_2=CH-CH=CH_2 \qquad III$$

(1,3-butadiene)

$$R^7CH=CH-CH=CHR^8 \qquad IV$$

wherein each one of $R^7$ and $R^8$, independently, is H or a $C_1$ to $C_3$ alkyl.

$$NC-CH_2-CH=CH-CH_3 \qquad V$$

(3PN)

$$CH_2=CH-CH_2-CH_2-CN \qquad VI$$

(4PN)

$$\begin{array}{c} CH_2=CH-CH-CH_3 \\ | \\ CN \end{array} \qquad VII$$

(2M3BN)

It will be recognized that Compound III is a special case of Formula IV, where each one of $R^7$ and $R^8$ is hydrogen.

In the practice of the hydrocyanation process of the present invention, a reactor, such as a tubular reactor, is charged in an inert atmosphere with the desired supported Ni(0) (Ligand) catalyst. The reactor feed and exit lines are preferably purged with an inert gas, such as $N_2$, Ar, or He. The reactor is then heated to the desired temperature, either under a continuous flow of inert gas or sealed from the ambient atmosphere. The reactor is fed with the desired diolefinic compound and HCN. These may be fed together or separately, either neat or as solutions in suitable solvents, such as acetonitrile or toluene. When the reactants are fed continuously, an inert gas carrier normally is employed as well. The diolefinic compound, HCN and any solvent are passed through a heated portion of feed line heated to the reaction temperature to ensure complete vaporization. The gaseous product mixture exiting the reactor can be passed, if desired, through a heated gas sampling loop of a gas chromatograph for perodically monitoring the progress of the reaction. Alternatively, the gaseous effluent can be cooled to about 0° C. to 25° C. in order to condense all products to liquids. The flow rate of the diolefinic compound preferably is such that its mole ratio to catalyst, per hour of continuous feed, is about 5:1 to 100:1. The mole ratio of the diolefinic compound to HCN normally is at least about 1:1.

The hydrocyanation reaction is preferably carried out without a solvent. If any solvent is used, the solvent should be gaseous at the reaction temperature and pressure and inert towards the diolefinic compound, HCN, and the catalyst. Such solvents include hydrocarbons such as hexane, benzene, or xylene, or nitriles such as acetonitrile.

EXAMPLES

This invention is now illustrated by the following non-limiting examples of certain preferred embodiments thereof, where all parts, proportions, and percentages are by weight, unless otherwise indicated. In the Examples, Ligand "A" is the ligand of Formula II, where each $R^4$ is $OCH_3$, and each $R^6$ is t-butyl.

EXAMPLE 1

Synthesis of a carbon-supported Ni(0)(Ligand "A")$CH_2$=$CH_2$, where the Ligand "A" is of Formula II, where each $R^4$ is $OCH_3$ and each $R^6$ is t-butyl All operations were carried out in a nitrogen atmosphere. Into a glass vial was placed 0.385 g (1.5 mmoles) of Ni(acetylacetonate)$_2$, 1.18 g (1.5 mmoles) of Ligand "A" and 20 mL toluene. Next, ethylene was bubbled through the solution. Then, 2.3 mL of a 1.9M (25%) solution of $(C_2H_5)_3Al$ (4.4 mmoles) in toluene was added dropwise, while ethylene still was being introduced into the solution. After several more minutes, the ethylene flow was stopped and the vial was sealed with a septum. The reaction contents were stirred overnight. The next day, about half of the solvent was removed by evaporation at a reduced pressure. A portion of the solid reaction product was recovered by filtration. Methanol was added to precipitate additional solid reaction product. Recovered solid product was dried under vacuum to yield 0.78 g of a gold-colored powder. A $^{31}P$ NMR spectrum of the final product exhibited a major singlet at 169.9 ppm {Ni(Ligand "A")$CH_2$=$CH_2$} and a minor singlet at 162.8 ppm {Ni(Ligand "A")$_2$}.

A 5-g sample of acid-washed carbon was heated to 100° C. in a quartz tube in a stream of nitrogen for 1 hour. The tube was cooled to room temperature, sealed, and transferred to a nitrogen-filled glove box. The dried carbon was stirred with a solution of 0.5 g (0.57 mmole) of {Ni(Ligand "A")$CH_2$=$CH_2$} in 10 mL of dry toluene for 30 minutes. Toluene was evaporated under vacuum to afford a dry {Ni(Ligand "A")$CH_2$=$CH_2$}/C catalyst.

EXAMPLES 2-5

Gas-Phase Hydrocyanation of Butadiene

An empty 0.25-inch (0.64 cm) diameter, 15-inch (37.5 cm) long stainless steel tubular reactor was placed in a nitrogen-filled glove box. A plug of glass wool was placed in the bottom end of the reactor, followed by the amount and type of Ni(0) catalyst shown in Table 1. A thermocouple was inserted into the top of the reactor. Both ends of the reactor were sealed with metal fittings, and the reactor was removed from the glove box and connected to stainless steel reactor feed lines purged with nitrogen. Attached to the outlet side of the reactor was a jacketed receiver cooled with ethylene glycol at 0° C. The condensed liquid products were periodically removed and analyzed by gas chromatography (GC). GC analyses were done on a 30 m DB-23 capillary column of a 0.32 mm integral diameter, supplied by J&W Scientific, Folsom, Calif. The stationary phase was cyanopropyl (50%) methylpolysiloxane. Also attached to the receiver was a line for continuously feeding an approximately 0.5% solution of 1-cyanooctane dissolved in acetonitrile, which served as an internal GC standard. The feed streams of nitrogen, butadiene, and HCN were preheated to 120° C. to ensure complete vaporization. The reactor was heated in a split tube furnace to the temperatures shown in Table 1. Product samples were collected, generally every hour. Table 1 shows the specific reaction conditions and summarizes the results.

that both reactants, as well as the solvent, were introduced into the reactor in the gas phase. The reaction gases were admitted to the reactor without exposing the catalyst to air.

Table 2 shows the specific reaction conditions and summarizes data for a representative experiment. The catalyst was a silica-supported Ni(0)(Ligand

TABLE 1

Gas Phase BD/HCN Runs

| Ex No. | Catalyst (Support) | Catalyst g, % Ni | Feed mmole/hr BD | Feed mmole/hr HCN | Feed cc/min N2 | Temp. °C. | Elapsed Time Min. | % Conv. to PN's | % Selectivity 3PN, 4PN, 2M3BN | % Conv. to VCH | % Conv. to DN's |
|---|---|---|---|---|---|---|---|---|---|---|---|
| 2 | NiL4 L = p-tritolylphosphite (Carbon) | 1.04, 1.14 | 6.9 | 7.5 | 10 | 150 | 60 | 0.05 | 100 | 0.0 | 0 |
|   |   |   |   |   |   | 150 | 120 | 0.18 | 100 | 8.0 | 0 |
|   |   |   |   |   |   | 150 | 180 | 0.07 | 100 | 8.4 | 0 |
|   |   |   |   |   |   | 160 | 240 | 0.08 | 100 | 12.5 | 0 |
|   |   |   |   |   |   | 160 | 300 | 0.07 | 100 | 10.2 | 0 |
| 3 | NiLCH$_2$=CH$_2$ L = Ligand "A" | 1.05, 0.34 | 6.9 | 7.5 | 10 | 150 | 60 | 0.52 | 87 | 0.0 | 0 |
|   |   |   |   |   |   | 150 | 120 | 2.04 | 92.1 | 0.0 | 0 |
|   |   |   |   |   |   | 150 | 180 | 4.82 | 92.1 | 0.3 | 0.03 |
|   |   |   |   |   |   | 170 | 240 | 7.15 | 92.6 | 15.4 | 0.05 |
|   |   |   |   |   |   | 170 | 300 | 4.90 | 94.8 | 10.0 | 0 |
|   | (Carbon) |   |   |   |   | 170 | 330 | 3.94 | 87.9 | 8.6 | 0.11 |
| 4 | NiL2 L = Ligand "A" | 1.09, 0.36 | 6.9 | 7.5 | 10 | 120 | 60 | 1.36 | 77.0 | 8.9 | 0 |
|   |   |   |   |   |   | 120 | 120 | 0.89 | 81.7 | 9.8 | 0 |
|   |   |   |   |   |   | 120 | 180 | 0.26 | 87.5 | 10.4 | 0 |
|   |   |   |   |   |   | 150 | 240 | 0.25 | 79.2 | 9.3 | 0 |
|   | (Alumina) |   |   |   |   | 150 | 300 | 0.07 | 75.0 | 11.9 | 0.1 |
| 5 | NiL2 L = Ligand "A" | 0.83, 0.36 | 6.9 | 7.5 | 10 | 140 | 60 | 19.40 | 69.8 | 5.5 | 0.99 |
|   |   |   |   |   |   | 140 | 120 | 1.60 | 19.3 | 6.8 | 3.67 |
|   |   |   |   |   |   | 120 | 180 | 0.30 | 6.0 | 8.2 | 3.52 |
|   |   |   |   |   |   | 120 | 240 | 0.08 | 4.4 | 8.6 | 1.22 |
|   | (Silica) |   |   |   |   | 140 | 300 | 0.13 | 9.6 | 8.7 | 0.93 |
|   |   |   |   |   |   | 140 | 360 | 0.14 | 13.8 | 9.0 | 0.65 |
|   |   |   |   |   |   | 140 | 420 | 0.13 | 17.2 | 9.3 | 0.48 |

In the above Table, percent conversion to PNs was calculated as (measured GC area % for PNs/GC area % for 1-cyanooctane)×(GC response factor for PNs)×(g of 1-cyanooctane fed per hour/mmoles of BD fed per hour)×100. Response factor is the number, characteristic for each compound, required for converting area percent to weight percent/molecular weight of PNs.

Percent conversion to DNs was determined as (measured GC area % for DNs)/(GC area % for 2-octyl cyanide)×(GC response factor for DNs)×(g of 2-octyl cyanide fed per hour./mmoles of BD fed per hour)×100.

Percent conversion to VCH was determined as (measured GC area % for VCH)/(GC area % for 2-octyl cyanide)×(g of 2-octyl cyanide fed per hour/mmoles of BD fed per hour)×100.

Percent selectivity to (3PN+4PN+2M3BN) was determined as (GC area % for 3PN+4PN+2M3BN)/(GC area % for PNs+DNs)×100.

EXAMPLE 6

Continuous Gas-Phase Hydrocyanation of Butadiene Monitored by On-Line GC Analysis The same reactor and procedures as described for Examples 2-5 were used but were adapted to the needs of the continuous, GC-monitored process. The feed and product effluent lines were purged with reaction gases. The exit line was connected to a gas chromatograph, both the line and the control valve being heated to 165° C. Both HCN and butadiene were first dissolved in toluene. The toluene solution, containing 1.87% HCN and 8.32% butadiene, was fed by means of a glass syringe injector pump through a line heated to 150° C., so "A")CH$_2$=CH$_2$, where Ligand "A" is represented by Formula II, where each R$^4$ is OCH$_3$, and each R$^6$ is t-butyl.

The flow of BD was 0.67 mmole/hr, and the flow of HCN was 0.30 mmole/hr. The flow of nitrogen was 10 mL/min.

TABLE 2

| Elapsed Time, hr | % Conv. BD | % Conv. to PNs | % Conv. to DNs | % Selectivity 3PN, 4PN, 2M3BN |
|---|---|---|---|---|
| 1.5 | 76.4 | 90.4 | — | 93.4 |
| 2.5 | 50.4 | 100.0 | — | 97.1 |
| 3.5 | 90.8 | 91.2 | — | 97.2 |
| 4.5 | 34.1 | 80.5 | — | 100.0 |
| 5.5 | 6.6 | 106.1 | 2.8 | 100.0 |
| 6.5 | 40.7 | 109.1 | 3.8 | 100.0 |
| 7.5 | 90.4 | 76.5 | 3.0 | 100.0 |
| 8.5 | 24.9 | 121.1 | 4.0 | 100.0 |
| 9.5 | 49.1 | 98.9 | 3.4 | 100.0 |
| 10.5 | 49.4 | 81.0 | 2.2 | 100.0 |
| 11.5 | 36.0 | 113.4 | 3.4 | 100.0 |
| 12.5 | 45.8 | 92.8 | 3.2 | 100.0 |
| 13.5 | 34.3 | 108.6 | 4.4 | 100.0 |
| 14.5 | 43.4 | 87.4 | 2.8 | 100.0 |
| 15.5 | 42.3 | 94.1 | 5.2 | 100.0 |
| 16.5 | 44.1 | 82.9 | 3.4 | 100.0 |
| 17.5 | 39.1 | 76.2 | 1.4 | 100.0 |
| 18.5 | 30.7 | 74.1 | 2.4 | 100.0 |
| 19.5 | 28.6 | 70.6 | 3.2 | 100.0 |
|   |   |   | 2.2 | 98.3 |

In the above Table, % conversion to BD was determined as (measured GC area % for BD)×(GC response factor for converting area % BD to weight % BD)×1/(theoretical weight % BD at 100% of BD conversion)×100. The theoretical maximum BD conversion was 45% (i.e., 0.30 mmole/hr HCN/0.67 mmole/hr BD=0.45).

Percent conversion to PNs was determined as (GC area % for PNs)×(GC response factor for converting area % for PNs to weight % of PNs)×1/(theoretical weight % of PNs at 100% conversion of HCN)×100.

Percent conversion to DNs was determined as (measured GC area % for DNs)×(GC response factor for converting area % DNs to weight % DNs)×1/(theoretical weight % DNs at 100% conversion of HCN to DNs).

Percent selectivity to (3PN+4PN+2M3BN) was determined as (GC area % for 3PN+4PN+2M3BN)/(GC area % for PNs+DNs)×100.

Table 2 shows that the catalyst employed remained reasonably effective during the testing period. In addition, from Tables 1 and 2 can be concluded that monodentate phosphite ligands are not as active or long-lived as bidentate phosphite ligands. Moreover, these Tables indicate that silica is a preferred support over alumina or carbon.

COMPARATIVE EXAMPLE 7

Gas-Phase Hydrocyanation of Butadiene in Accordance with U.S. Pat. No. 3,547,942, without additional feed of HCl In an aluminum crucible were mixed 16.0 g (40.0 mmoles) of $Cr(NO_3)_3 \cdot 9H_2O$, 2.0 g (6.8 mmoles) of $Cu(NO_3)_2 \cdot 6H_2O$, and 4.0 g (13.5 mmoles) of $Zn(NO_3)_2 \cdot 6H_2O$. The mixture was moistened with water to a stiff paste and was heated in a muffle furnace from room temperature to 600° C. in 4 hours. The crucible was kept at 600° C. for 16 hours, then was cooled to room temperature. The dry reaction product was zinc copper chromite, which then was used as the catalyst. The 0.25-inch (0.64 cm) diameter reactor was charged with 1.11 g of the above zinc copper chromite catalyst. The reactor system described for Examples 2–7 was used under the conditions shown in Table 1. No pentenenitrile products were detected.

TABLE 3

| mmoles/hr | | $N_2$ ml/min. | Temp., °C. | Elapsed Sample time, hr |
|---|---|---|---|---|
| Butadiene | HCN | | | |
| 6.9 | 7.5 | 15 | 200 | 1 |
| 6.9 | 7.5 | 15 | 200 | 2 |
| 6.9 | 7.5 | 15 | 250 | 3 |
| 6.9 | 7.5 | 15 | 250 | 4 |
| 6.9 | 7.5 | 15 | 300 | 5 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for the gas-phase hydrocyanation of diolefinic compounds comprising, reacting an acylic, aliphatic, conjugated diolefinic compound with HCN in the gas phase within a temperature range of 135° C. to 170° C. in the presence of a supported catalyst composition comprising zero-valent nickel and at least one bidentate phosphite ligand selected from the group represented by Formulas I and II:

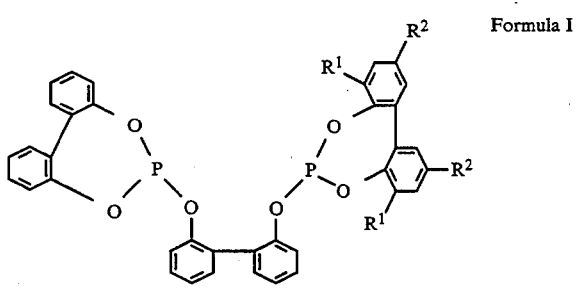

Formula I wherein
each $R^1$, independently, is a secondary or tertiary hydrocarbyl of 3 to 12 carbon atoms;
each $R^2$, independently, is H, a $C_1$ to $C_{12}$ alkyl, or $OR^3$, wherein $R^3$ is $C_1$ to $C_{12}$ alkyl; and

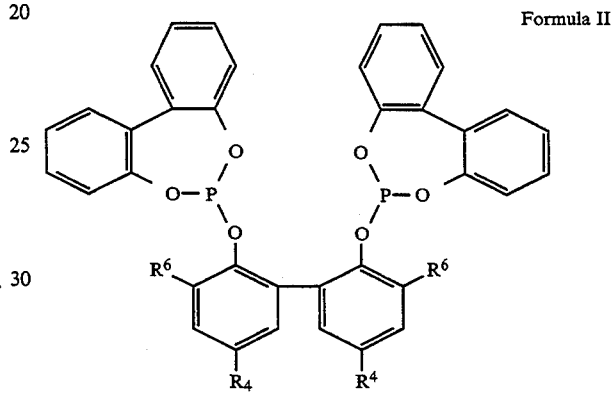

Formula II wherein
each $R^4$, independently, is a tertiary hydrocarbon of up to 12 carbon atoms, or $OR^5$, wherein $R^5$ is a $C_1$ to $C_{12}$ alkyl; and
each $R^6$, independently, is a tertiary hydrocarbon of up to 12 carbon atoms, to produce acyclic olefinic nitriles in which the olefinic double bond is not conjugated with the cyano group.

2. The process of claim 1 wherein the catalyst support is selected from the group consisting of silica, alumina, and carbon.

3. The process of claim 2 wherein the support is silica.

4. The process of claim 1 wherein the reaction is carried out at a temperature of 140°–160° C.

5. The process of claim 4 wherein the reaction is carried out at a temperature of 145°–150° C.

6. The process of claim 1 wherein the starting diolefinic compound is a diolefin represented by the following Formula IV

$R^7CH=CH-CH=CHR^8$    IV wherein each one of $R^7$ and $R^8$, independently, is H or a $C_1$ to $C_3$ alkyl.

7. The process of claim 6 wherein the starting diolefinic compound is 1-3-butadiene.

8. The process of claim 1 wherein the starting diolefinic compound is substituted with at least one other group which does not deactivate the catalyst.

9. The process of claim 7 wherein HCN and 1,3-butadiene are introduced into the reaction without a solvent or diluent.

10. The process of claim 7 wherein at least one of HCN and 1,3-butadiene is dissolved in a solvent, inert to the starting materials and to the catalyst under the reaction conditions, prior to being introduced into the reaction, but the solution is vaporized prior to its entry into the reaction.

11. The process of claim 1 which is a continuous process.

12. The process of claim 1 which is a batch process.

13. The process of claim 11 wherein the flow rate of the diolefinic compound is such that its mole ratio to the catalyst, per hour of continuous feed is between 5:1 and 100:1.

14. The process of claim 1 wherein the mole ratio of diolefinic compound to HCN is at least 1:1.

15. The process of claim 1 which is conducted at a pressure within the range of 101.3 to 1013 kPa.

* * * * *